United States Patent [19]
Joosten

[11] 4,433,582
[45] Feb. 28, 1984

[54] DAMPING DEVICE FOR USE WITH ACOUSTIC INFORMATION GENERATION MACHINES

[75] Inventor: Michael W. Joosten, Ponca City, Okla.

[73] Assignee: Conoco Inc., Ponca City, Okla.

[21] Appl. No.: 267,109

[22] Filed: May 26, 1981

[51] Int. Cl.³ .................. B32B 15/04; G01N 3/20; G01N 29/04
[52] U.S. Cl. ........................... 73/788; 73/799; 73/801; 73/852; 73/856; 148/402; 181/207; 248/638; 369/263
[58] Field of Search ............... 73/788, 799, 801, 852, 73/853, 856; 181/202, 207; 369/263, 266; 248/634, 635, 638; 148/402; 428/960

[56] References Cited
U.S. PATENT DOCUMENTS

| | | | |
|---|---|---|---|
| 2,083,037 | 6/1937 | Schmittgen | 369/266 |
| 3,194,063 | 7/1965 | McKean | 73/852 |
| 4,190,131 | 2/1960 | Robinson | 181/207 |

FOREIGN PATENT DOCUMENTS 2724539  11/1978  Fed. Rep. of Germany ...... 428/960

OTHER PUBLICATIONS

Jackson, C. M. et al., 55 Mitinol-The Alloy with a Memory, etc., A Report, NASA-SP5110, pp. 35–42, 1972.

*Primary Examiner*—Steven L. Stephan
*Attorney, Agent, or Firm*—A. Joe Reinert

[57] ABSTRACT

A damping device for use with acoustic information generation machines for isolating a generation portion of the generation device from contamination by extraneous acoustic emissions. A metal isolation piece consisting of a shape-memory alloy is disposed between an extraneous noise source and the generation portion of the device. Acoustic information generation devices in accordance with the present invention include phonograph record playing devices and testing devices for recording acoustic signals generated upon stressing a test piece. Thus, the present invention provides improved phonograph record playing devices and an improved testing device.

2 Claims, 4 Drawing Figures

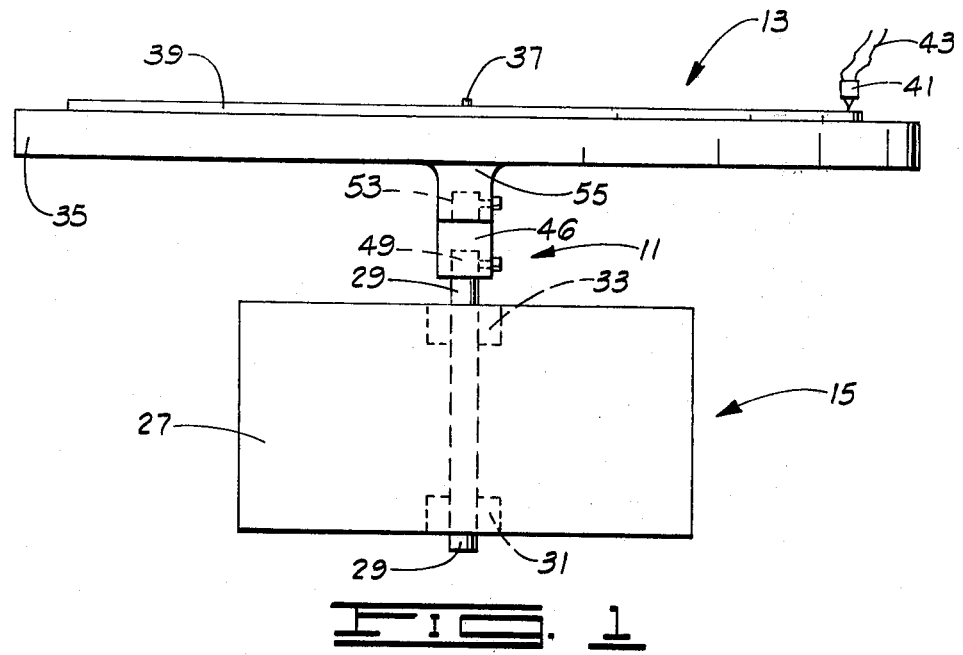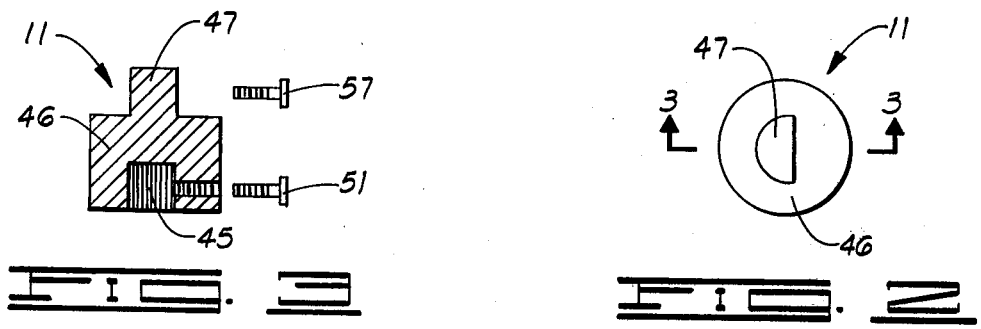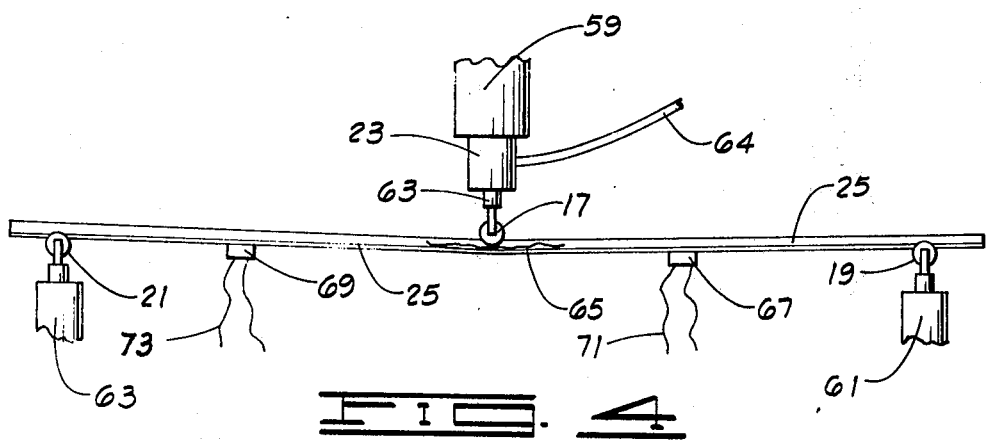

DAMPING DEVICE FOR USE WITH ACOUSTIC INFORMATION GENERATION MACHINES

BACKGROUND OF THE INVENTION

1. Field of the Invention

The present invention relates in general to acoustic information generation machines and more particularly to damping devices and acoustic vibration filters for use with acoustic information generation machines.

2. Background of the Invention

In the past, acoustic vibration has been utilized to carry information in a variety of circumstances. A classic example of an acoustic information generation machine is a phonograph record player. A phonograph record has grooves with predetermined waves formed therein. These waves carry information, such as music, which is transmitted to a stylus in the form of acoustic vibration of the stylus. Rotation of the phonograph record so that the stylus tracks in the grooves generates the acoustic information which is then ultimately converted to an amplified sound.

Another example of an acoustic information generation machine is a testing device which generates cracks in a pipe so that the crack initiation propagation can be recorded. The information on crack behavior in the pipe material is useful in evaluating the pipe and the pipe material. Machines of this type apply a stress on a pipe to initiate and propagate a crack in the pipe. Typically, a hydraulic piston is hydraulically actuated to exert a radial force on a midportion of the pipe. The ends of the pipe are supported to oppose this force. As the crack propagates due to this bending force, the pipe emits accoustic signals and this information is recorded and analyzed to evaluate the crack propagation.

A particular problem in acoustic information generation machines of the past has been isolating extraneous acoustic signals from the machine. For example, in the playing of a phonograph record, it is important that the only vibrations transmitted through the stylus from the record be those produced by the waves in the grooves. If the phonograph record is vibrated from outside sources, these vibrations will be transmitted to the stylus distorting the music which is amplified. A particularly troublesome source for these extraneous vibrations is the motor which rotates the phonograph record and the bearings which support the phonograph record and turntable during rotation.

In the testing device described above extraneous vibration is often recorded along with the signals produced by the crack propagation distorting the information concerning crack behavior. A typical source for the extraneous vibration in the testing device is the hydraulic piston which stresses the pipe. Other sources of extraneous acoustic emission are the bearing surfaces of the pipe supports.

In the past, a typical solution for reducing the amount of extraneous acoustic vibration transmitted to the acoustic information generation machine is to introduce a rubber piece between the extraneous source of vibration and the acoustic information generation point. For example, in phonograph record players often the motor is connected to the phonograph record turntable through a rubber belt which extends from a motor shaft to a turntable shaft. In this way, the motor vibration is isolated from the turntable. However, a disadvantage of using rubber is that rubber tends to wear out quickly, requiring replacement of the rubber belt. Furthermore, the rubber can become stiff with age, reducing its ability to isolate the extraneous vibration. When too resilient, the rubber belt can stretch or slip causing the turntable platter to lag behind the motor. Finally, a rubber belt positioned as described above does not isolate the bearing vibration transmitted from the turntable shaft bearing to the turntable.

In the test device rubber is an unsatisfactory way to isolate the extraneous acoustic vibration from the test piece because rubber cannot withstand the stresses necessary to produce a crack propagation in the pipe. Accordingly, an alternative method has been used to prevent the recording of erroneous information. This alternative consists of positioning acoustic sensors (for example, transducers) adjacent each of the supports and the hydraulic cylinders so that acoustic signals coming from these sources will be detected. By simultaneously comparing the signals received by sensors located away from these points, it can be determined whether the signal is being received solely from the crack propagation or from extraneous sources as well. When extraneous sources are producing vibration which distorts the recording of crack propagation vibration, the recording can be stopped. Thus, only true crack propagation acoustic vibration is recorded.

A disadvantage with the "lock-out" transducers or sensors used for halting the recording during extraneous vibration is that only part of the crack propagation information is received. That information generated during a non-recorded period is lost. Furthermore, this method of using lockout transducers requires expensive equipment to compare the acoustic information from the lock-out transducers with the acoustic information received by the crack propagation transducers.

Recently, shape-memory alloys have been discovered which have the unusual property of recovering their predeformation shape after they have been heated from a lower temperature at which a deformation occurred. This material is described in U.S. Pat. No. 4,149,911 to Clabburn. A particular, although unexplained, property of many of these shape-memory alloys is that they damp vibrations. These damping characteristics are particularly high in the austenitic phase of the alloy. In the past, however, shape-memory alloys have not been utilized for a damping material.

SUMMARY OF THE INVENTION

It is an object of the present invention to provide a device for damping acoustic emissions transmitted from a acoustically noisy energy source to a work piece from which information carrying acoustic emission is received. In particular, it is an object to damp such emissions to prevent contamination of the acoustic emissions generated at the work piece.

It is also an object of the present invention to provide a device for damping acoustic emissions transmitted through an energy-carrying member to an acoustic information generation device. In particular, an object is to provide such a device which is strong and long-lasting.

Another object of the present invention is to provide an improved phonograph record playing device which prevents extraneous acoustic vibration from being transmitted to the phonograph turntable.

Still a further object of the present invention is to provide an improved testing device for stressing a test member which prevents extraneous acoustic vibration from entering the test member. Particularly, it is an object to prevent the contamination of acoustic information received from the test member without reducing the amount of useful acoustic information received from the test member.

In accordance with these objects a device for damping acoustic emissions transmitted through an energy-carrying member to an acoustic information generation device is provided. A metal isolation piece consisting of a shape-memory alloy is disposed along the energy-carrying member so that acoustic emissions transmitted through the energy-carrying member must encounter the metal isolation piece. Acoustic emissions encountering the shape-memory metal isolation piece are damped so that extraneous acoustic emissions do not contaminate the acoustic generation.

Preferably, the metal isolation piece consists essentially of an austenitic phase of the shape-memory alloy. Also preferably the shape-memory alloy is selected from the group consisting of NiTi, Fe$_3$Pt, Cu-Al-Ni, Cu-Zn-Al, InTl, CuSn, Ni-Al, Cu-Ni-X, and Ni-Ti-X (wherein X is an alloying element).

An improved phonograph record playing device is provided by the present invention utilizing a metal connection means directly connecting a motor shaft to a turntable platter so that rotation of the motor shaft is directly transmitted to the turntable platter through the metal connection means. The metal connection means includes a metal isolation piece consisting of a shape-memory alloy and disposed so that acoustic emissions transmitted through the metal connection means to the turntable platter must encounter the metal isolation piece. In this manner, extraneous vibrations from the motor and motor shaft bearings are prevented from entering the turntable platter and contaminating music as the phonograph record is played.

The present invention provides an improved testing device for stressing a test member producing acoustic information from the test member related to changes occurring in the test member, such as crack propagation. The test device includes a stress member for contacting the test member and applying the stress to produce a crack. A metal isolation piece consisting of a shape-memory alloy is disposed along the stress member so that acoustic emissions transmitted through the stress member must encounter the metal isolation piece. In this manner, extraneous acoustic vibrations are prevented from entering the test member so that acoustic information received from the test member is not contaminated and relates to crack propagation, for example.

For a further understanding of the invention and further objects, features, and advantages thereof, reference may now be had to the following description taken in conjunction with the accompanying drawings.

BRIEF DESCRIPTION OF THE DRAWINGS

FIG. 1 is a side schematic view of a phonograph record playing device constructed in accordance with the present invention.

FIG. 2 is a top plan view of a piece of the device shown in FIG. 1.

FIG. 3 is a side cross-sectional view taken along the lines shown in FIG. 2 of the element shown in FIG. 2.

FIG. 4 is a side schematic view of a testing device constructed in accordance with the present invention.

DESCRIPTION OF THE PREFERRED EMBODIMENT

Referring now to FIGS. 1 through 4, the present invention can be broadly described as an acoustic information generation device and a device for damping extraneous acoustic vibration within the acoustic information generation device. Broadly, the damping device isolates the acoustical emissions transmitted from an energy or force-carrying member to a work piece. As shown in FIG. 1, a damping device 11 isolates the work piece 13 from the force member 15. As shown in FIG. 4, the damping devices 17, 19 and 21 isolate the force-carrying member 23 from the work piece 25.

Referring now to FIGS. 1, 2 and 3, a phonograph record playing device constructed in accordance with the present invention is shown. The phonograph record playing device has a motor 27 used for rotating a motor shaft 29 mounted on bearings 31 and 33. The motor 27 is conventional and the details of this motor are not described because they are well known to those skilled in the art of phonograph record construction.

A turntable platter 35 is connected to motor shaft 29 so that turntable 35 can be powered by motor 27. Connected to the upper center of turntable 35 is a pin 37 which is received in the center of a phonograph record 39 when the record is mounted on the turntable 35.

A stylus 41 is provided to track the grooves of the phonograph record 39 producing acoustic vibrations which are converted to electrical information transmitted through wires 43 attached to stylus 41. Rotation of the phonograph record 39 generates the acoustic vibrations in stylus 41 due to recorded waves formed in the record 39.

Mounted on the end of shaft 29 is a coupling 46. Coupling 46 has a spline-receiving slot 45 for receiving the splined end 49 of shaft 29. A keyway 47 is provided on the upper end of coupling 46 to be received in a slot 53 in the lower end of a mounting bar 55 at the lower center of turntable 35. A set screw 51 is threaded through the side of coupling 46 to fix the spline 49 to coupling 46. A set screw 57 is received through mounting bar 55 to fix the keyway 47 to the turntable 35.

Thus, in the present invention the shaft 29 is directly mounted to the turntable 35 through a coupling 46. No belt or rubber connection is used as provided in the prior art. In this manner the turntable platter 35 is directly driven by the motor shaft 29 without undesirable rubber pieces interposed therebetween. This mechanical direct connection between motor 27 and turntable 35 is durable and almost instantly responsive to the power supplied by motor 27.

The coupling 46 consists of a shape-memory alloy. It has been determined that shape-memory alloys have a significant damping effect on acoustic vibrations and, therefore, acoustic vibrations which encounter coupling 46 are damped. It can be seen that coupling 46 isolates turntable 35 from the motor shaft 29 so that all acoustic emissions generated in the motor 27 and bearings 31 and 33 must encounter coupling 46. This prevents extraneous or contaminating acoustic emissions from entering turntable platter 35 through the motor shaft 29.

It has been discovered that the following group of shape-memory alloys are particular suitable for use in coupling 46: NiTi, Fe$_3$Pt, Cu-Al-Ni, Cu-Zn-Al, InTl, CuSn, Ni-Al, Cu-Ni-X, and Ni-Ti-X, (where X ia an alloying element). Each of these shape-memory alloy metals has a high damping characteristic. Furthermore, each of these metal alloys are relatively inexpensive.

It has also been found that the shape-memory alloys described above have a higher damping characteristic when the alloy is in an austenitic phase. Therefore, it is preferable to construct the coupling 46 of an austenitic phase of the shape-memory alloy. Of course, since shape-memory alloys change from an austenitic phase to a martensitic phase at certain temperatures, depending upon their composition, it is necessary to choose compositions which have an austenitic phase at room temperature in order to construct the coupling 46 of an austenitic phase of the shape-memory alloy. The compositions of shape-memory alloys and the transition temperatures from martensitic to austenitic phases of these compositions are well known to those skilled in the art.

Referring now to FIG. 4, a test device constructed in accordance with the present invention is shown. In general, the test device is provided for bending a pipe 25 which produces acoustic information. To bend the pipe 25 three secured beams 59, 61 and 63 are fixed below the ends of the pipe 25. Mounted on beams 61 and 63 are rollers 19 and 21 which receive the ends of the pipe. These rollers 19 and 21 are curved so that the pipe will not move laterally off of the rollers. Bearings are provided at the journaled point between the rollers 19 and 21 and the beams 61 and 63, respectively. The bearings and the shape of the rollers are conventional.

Mounted beneath beam 59 is a hydraulic cylinder 23. This hydraulic cylinder has a piston 63 which is driven by the hydraulic cylinder 23. A hydraulic fluid conduit 64 supplies hydraulic fluid to and from the hydraulic cylinder 23. A source of powering the hydraulic fluid through the conduit 64 is provided, but not shown in the FIG. Mounted to the hydraulic piston 64 is a roller 17. This roller 17 is shaped like rollers 19 and 21 to receive the pipe 25. Likewise, it is journaled to the hydraulic piston 63 in a conventional manner.

In operation, a pipe 25 is positioned between rollers 17, 19 and 21. Hydraulic fluid is supplied through conduit 64 to hydraulic cylinder 23. This causes the hydraulic piston 63 to move downwardly bending the pipe 25 about its mid-point. Rollers 19 and 21 support the ends of the pipe in opposition to the bending force supplied by roller 17.

As the pipe 25 bends, a crack 65 propagates along the pipe 25. Propagation of the crack 65 creates acoustic emissions which are received by transducers 67 and 69 mounted on mid-portions of the pipe between the roller 17 and the rollers 19 and 21. The acoustic emissions transducers 67 and 69 convert the acoustic emissions from the crack propagation to electrical impulses which are transmitted through wires 71 and 73.

In the prior art, lock-out transducers were placed on the pipe 25 adjacent rollers 19 and 21 and on either side of roller 17. By utilizing equipment to compare the signals received from the lock-out transducers and the transducers 67 and 69 it could be determined when extraneous acoustic emissions were entering pipe 25 through rollers 17, 19 and 21. When such extraneous acoustic emissions were determined to be present, the signals from transducers 67 and 69 were blocked. In this manner, contaminated information was not recorded.

The present invention avoids the introduction of extraneous acoustic emissions through rollers 17, 19 and 21 by constructing the rollers 17, 19 and 21 of a shape-memory alloy. As with the coupling 46, it is desirable to construct the rollers 17, 19 and 21 of an alloy selected from the group consisting of Ni, Fe$_3$Pt, Cu-Al-Ni, Cu-Zn-Al, InTl, CuSn, Ni-Al, Cu-Ni-X, and Ni-Ti-X (where X is an alloying element).

Also, it is preferable to provide the shape-memory alloy in an austenitic phase.

Because the rollers 17, 19 and 21 consist of a shape-memory alloy, acoustic emissions from the hydraulic cylinder 23 and from the bearings at rollers 17, 19 and 21 are damped before they can reach pipe 25. This prevents the contamination of acoustic emissions due to the crack propagation. Lock-out or blocking of information is not required.

Thus, the damping device for use with acoustic information generation machines of the present invention is well adapted to attain the objects and advantages mentioned above as well as those inherent therein. While presently preferred embodiments of the invention have been described for the purpose of this disclosure, numerous changes in the construction and arrangement of parts can be made by those skilled in the art which changes are encompassed within the spirit of this invention as defined by the appended claims.

The foregoing disclosure and the showings made in the drawings are merely illustrative of the principles of this invention and are not to be interpreted in a limiting sense.

What is claimed is:

1. An improved testing device for stressing a test member producing acoustic information from the test member relating to changes occurring in the test member due to the stressing of the test member, of the type having at least one stress for contacting the test member and applying a stress thereto, the improvement comprising:

a metal isolation piece comprising a shape-memory alloy (an alloy having the capacity to regain its shape upon heating after deformation) disposed along the stress member so that acoustic emissions transmitted through said stress member must encounter said metal isolation piece, said metal isolation piece having resistance to deformation, wherein said metal isolation piece is disposed for contacting the test member and applying a stress thereto, wherein said metal isolation piece comprises a roller mounted on the end of the stress member, wherein said metal isolation piece consist essentially of an austenitic phase of said shape-memory alloy, and wherein said testing device further includes at least two other stress members disposed for contacting the test member and opposing the stress applied by at least one stress member so that a binding force can be applied to the test member;

each of at least two other stress members having mounted on the end thereof a roller for contacting the test member, said roller consisting essentially of an austenitic phase of a shape-memory alloy.

2. The device of claim 1 wherein each of said rollers consists of a shape-memory alloy selected from the group consisting of NiTi, Fe$_3$Pt, Cu-Al-Ni, Cu-Zn-Al, InTl, CuSn, Ni-Al, Cu-Ni-X, and Ni-Ti-Z, wherein X is an alloying element.

* * * * *